(12) United States Patent
Wang et al.

(10) Patent No.: US 8,889,945 B2
(45) Date of Patent: Nov. 18, 2014

(54) ELASTIC FILM CONTAINING A RENEWABLE STARCH POLYMER

(75) Inventors: James H. Wang, Appleton, WI (US); Bo Shi, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 911 days.

(21) Appl. No.: 12/962,749

(22) Filed: Dec. 8, 2010

(65) Prior Publication Data

US 2012/0150137 A1 Jun. 14, 2012

(51) Int. Cl.
| | |
|---|---|
| *A61F 13/15* | (2006.01) |
| *A61F 13/49* | (2006.01) |
| *C08L 23/14* | (2006.01) |
| *C08L 75/08* | (2006.01) |

(Continued)

(52) U.S. Cl.
CPC ....... *C08L 23/0807* (2013.01); *A61F 13/49017* (2013.01); *C08J 2323/08* (2013.01); *B29C 55/143* (2013.01); *A61F 13/4902* (2013.01); *C08L 23/14* (2013.01); *B29C 47/0057* (2013.01); *B29K 2067/003* (2013.01); *C08J 2403/02* (2013.01); *C08L 75/08* (2013.01); *B29K 2067/043* (2013.01); *B29K 2105/0038* (2013.01); *C08L 67/02* (2013.01); *C08L 3/02* (2013.01); *A61F 13/49011* (2013.01); *C08G 18/76* (2013.01); *B29C 55/005* (2013.01); *B29C 47/0021* (2013.01); *C08L 67/00* (2013.01); *B29C 47/065* (2013.01); *B29K 2995/006* (2013.01); *B29K 2077/00* (2013.01); *B29K 2067/046* (2013.01); *B29C 55/06* (2013.01); *B29C 47/8865* (2013.01); *B29K 2003/00* (2013.01); *C08L 23/16* (2013.01); *C08J 5/18* (2013.01); *B29C 47/0004* (2013.01); *B29K 2105/04* (2013.01); *B29K 2021/003* (2013.01)
USPC .......................... 604/364; 604/367; 604/370

(58) Field of Classification Search
USPC ......................................... 604/364, 367, 370
See application file for complete search history.

(56) References Cited

U.S. PATENT DOCUMENTS

| | | |
|---|---|---|
| 3,354,506 A | 11/1967 | Raley |
| 3,650,649 A | 3/1972 | Schippers |

(Continued)

FOREIGN PATENT DOCUMENTS

| | | |
|---|---|---|
| WO | WO 9516425 A2 | 6/1995 |
| WO | WO 9520615 A1 | 8/1995 |

(Continued)

OTHER PUBLICATIONS

Search Report and Written Opinion for PCT/IB2011/054830 dated Jun. 29, 2012, 11 pages.

(Continued)

*Primary Examiner* — Lynne Anderson
(74) *Attorney, Agent, or Firm* — Dority & Manning, P.A.

(57) ABSTRACT

A film that contains a thermoplastic composition having a substantial portion of a renewable, natural starch polymer, and yet is elastic and exhibits good strength properties, is provided. Although starch is normally chemically incompatible with most elastomeric polymers due to their different polarities, the present inventors have discovered that phase separation may be minimized by selectively controlling certain aspects of the film, such as the nature of the elastomeric polymer and the starch polymer, and other film components, the relative amount of the film components, and the process for making the film.

27 Claims, 2 Drawing Sheets

(51) Int. Cl.

| | | |
|---|---|---|
| *C08L 67/02* | (2006.01) | |
| *C08L 3/02* | (2006.01) | |
| *C08G 18/76* | (2006.01) | |
| *C08L 67/00* | (2006.01) | |
| *C08L 23/08* | (2006.01) | |
| *C08L 23/16* | (2006.01) | |
| *C08J 5/18* | (2006.01) | |
| *B29C 55/14* | (2006.01) | |
| *B29C 47/00* | (2006.01) | |
| *B29K 67/00* | (2006.01) | |
| *B29K 105/00* | (2006.01) | |
| *B29C 55/00* | (2006.01) | |
| *B29C 47/06* | (2006.01) | |
| *B29K 77/00* | (2006.01) | |
| *B29C 55/06* | (2006.01) | |
| *B29C 47/88* | (2006.01) | |
| *B29K 105/04* | (2006.01) | |
| *B29K 21/00* | (2006.01) | |

(56) References Cited

U.S. PATENT DOCUMENTS

| | | |
|---|---|---|
| 3,801,429 A | 4/1974 | Schrenk et al. |
| 3,963,656 A | 6/1976 | Meisert et al. |
| 4,323,534 A | 4/1982 | DesMarais |
| 4,663,220 A | 5/1987 | Wisneski et al. |
| 4,704,116 A | 11/1987 | Enloe |
| 4,789,699 A | 12/1988 | Kieffer et al. |
| 4,798,603 A | 1/1989 | Meyer et al. |
| 4,834,738 A | 5/1989 | Kielpikowski et al. |
| 4,873,270 A | 10/1989 | Aime et al. |
| 4,886,512 A | 12/1989 | Damico et al. |
| 4,937,299 A | 6/1990 | Ewen et al. |
| 4,940,464 A | 7/1990 | Van Gompel et al. |
| 5,093,422 A | 3/1992 | Himes |
| 5,158,810 A * | 10/1992 | Oishi et al. ............ 428/35.4 |
| 5,176,668 A | 1/1993 | Bernardin |
| 5,176,672 A | 1/1993 | Bruemmer et al. |
| 5,192,606 A | 3/1993 | Proxmire et al. |
| 5,218,071 A | 6/1993 | Tsutsui et al. |
| 5,234,978 A * | 8/1993 | Delrue et al. ............ 524/53 |
| 5,272,236 A | 12/1993 | Lai et al. |
| 5,278,272 A | 1/1994 | Lai et al. |
| 5,292,783 A | 3/1994 | Buchanan et al. |
| 5,296,229 A | 3/1994 | Grandjean |
| 5,304,599 A | 4/1994 | Himes |
| 5,322,728 A | 6/1994 | Davey et al. |
| 5,332,613 A | 7/1994 | Taylor et al. |
| 5,393,804 A * | 2/1995 | George et al. ............ 523/128 |
| 5,399,219 A | 3/1995 | Roessler et al. |
| 5,446,079 A | 8/1995 | Buchanan et al. |
| 5,472,775 A | 12/1995 | Obijeski et al. |
| 5,486,166 A | 1/1996 | Bishop et al. |
| 5,490,846 A | 2/1996 | Ellis et al. |
| 5,509,915 A | 4/1996 | Hanson et al. |
| 5,539,056 A | 7/1996 | Yang et al. |
| 5,540,796 A | 7/1996 | Fries |
| 5,558,659 A | 9/1996 | Sherrod et al. |
| 5,559,171 A | 9/1996 | Buchanan et al. |
| 5,571,619 A | 11/1996 | McAlpin et al. |
| 5,580,911 A | 12/1996 | Buchanan et al. |
| 5,595,618 A | 1/1997 | Fries et al. |
| 5,596,052 A | 1/1997 | Resconi et al. |
| 5,599,858 A | 2/1997 | Buchanan et al. |
| 5,605,961 A | 2/1997 | Lee et al. |
| 5,649,916 A | 7/1997 | DiPalma et al. |
| 5,695,868 A | 12/1997 | McCormack |
| 5,766,389 A | 6/1998 | Brandon et al. |
| 5,817,721 A | 10/1998 | Warzelhan et al. |
| 5,900,322 A | 5/1999 | Buchanan et al. |
| 6,008,276 A | 12/1999 | Kalbe et al. |
| 6,090,325 A | 7/2000 | Wheat et al. |
| 6,110,158 A | 8/2000 | Kielpikowski |
| 6,258,924 B1 | 7/2001 | Warzelhan et al. |
| 6,410,096 B1 | 6/2002 | Eggink et al. |
| 6,417,313 B2 | 7/2002 | Spyrou |
| 6,500,563 B1 | 12/2002 | Datta et al. |
| 6,511,465 B1 | 1/2003 | Freiburger et al. |
| 6,645,190 B1 | 11/2003 | Olson et al. |
| 6,663,611 B2 | 12/2003 | Blaney et al. |
| 6,709,526 B1 | 3/2004 | Bailey et al. |
| 6,753,384 B2 | 6/2004 | Whitehouse et al. |
| 6,761,711 B1 | 7/2004 | Fletcher et al. |
| 6,794,023 B1 | 9/2004 | Melik et al. |
| 6,821,612 B1 | 11/2004 | Melik et al. |
| 6,824,734 B2 | 11/2004 | Boggs et al. |
| 6,844,380 B2 | 1/2005 | Favis et al. |
| 6,888,044 B2 | 5/2005 | Fell et al. |
| 7,045,650 B2 | 5/2006 | Lawrey et al. |
| 7,071,249 B2 * | 7/2006 | Ho et al. ............ 524/39 |
| 7,153,569 B2 | 12/2006 | Kaufman et al. |
| 7,166,343 B2 | 1/2007 | Noda et al. |
| 7,208,535 B2 | 4/2007 | Asrar et al. |
| 7,776,020 B2 | 8/2010 | Kaufman et al. |
| 7,998,888 B2 | 8/2011 | Shi et al. |
| 2004/0060112 A1 | 4/2004 | Fell et al. |
| 2005/0245162 A1 | 11/2005 | McCormack et al. |
| 2006/0004193 A1 | 1/2006 | Muller et al. |
| 2006/0135728 A1 | 6/2006 | Peerlings et al. |
| 2006/0149199 A1 | 7/2006 | Topolkaraev et al. |
| 2007/0049719 A1 | 3/2007 | Brauer et al. |
| 2007/0082982 A1 * | 4/2007 | Noda et al. ............ 524/47 |
| 2007/0117931 A1 | 5/2007 | Inoue et al. |
| 2007/0275024 A1 * | 11/2007 | Hedley et al. ............ 424/405 |
| 2008/0147034 A1 * | 6/2008 | Wang et al. ............ 604/370 |
| 2009/0286031 A1 | 11/2009 | Shi et al. |
| 2009/0286906 A1 | 11/2009 | Shi et al. |

FOREIGN PATENT DOCUMENTS

| | | |
|---|---|---|
| WO | WO 9731979 A1 | 9/1997 |
| WO | WO 2008049099 A1 | 4/2008 |
| WO | WO 2008142139 A1 | 11/2008 |

OTHER PUBLICATIONS

ASTM D 1238-04c—*Standard Test Method for Melt Flow Rates of Thermoplastics by Extrusion Plastometer*, current edition approved Dec. 1, 2004, originally approved in 1965, pp. 1-14.

ASTM D 1525-07—*Standard Test Method for Vicat Softening Temperature of Plastics*, current edition approved Mar. 1, 2007, originally approved in 1958, pp. 1-9.

ASTM D 3418-03 (D 3417-99)—*Standard Test Method for Transition Temperatures and Enthalpies of Fusion and Crystallization of Polymers by Differential Scanning Calorimetry*, current edition approved Dec. 1, 2003, originally approved in 1975, pp. 66-72.

ASTM D 5034-95—*Standard Test Method for Breaking Strength and Elongation of Textile Fabrics (Grab Test)*, current edition approved May 15, 1995, pp. 674-681.

\* cited by examiner

ELASTIC FILM CONTAINING A RENEWABLE STARCH POLYMER

BACKGROUND OF THE INVENTION

Films are employed in a wide variety of disposable goods, such as diapers, sanitary napkins, adult incontinence garments, bandages, etc. For example, many diapers employs a backsheet that is formed from a plastic film (e.g., linear low density polyethylene) laminated to a nonwoven web. In some cases, the plastic film may contain an elastomeric component, such as a styrenic block copolymer (e.g., styrene-ethylene butylene-styrene ("S-EB-S") copolymers). One problem with such films, however, is that the polymers are not generally environmentally friendly or renewable. Moreover, because many renewable components are very stiff in nature, their use in elastic films is has been limited due to the need to maintain a high level of elongation, deformation recovery, and strength properties. As such, a need currently exists for an improved film that is both elastic and contains a renewable component.

SUMMARY OF THE INVENTION

In accordance with one embodiment of the present invention, an elastic film is disclosed that comprises a thermoplastic composition comprising at least one starch polymer constituting from about 1 wt. % to about 30 wt. % of the polymer content of the film and at least one elastomeric polymer constituting from about 30 wt. % to about 95 wt. % of the polymer content of the film, and at least one plasticizer constituting from about 0.1 wt. % to about 30 wt. % of the film. The weight ratio of elastomeric polymers to starch polymers in the film is from about 1 to about 10. The elastic film also exhibits an elongation in the machine direction and cross-machine direction of about 250% or more.

Other features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

Figure 1:
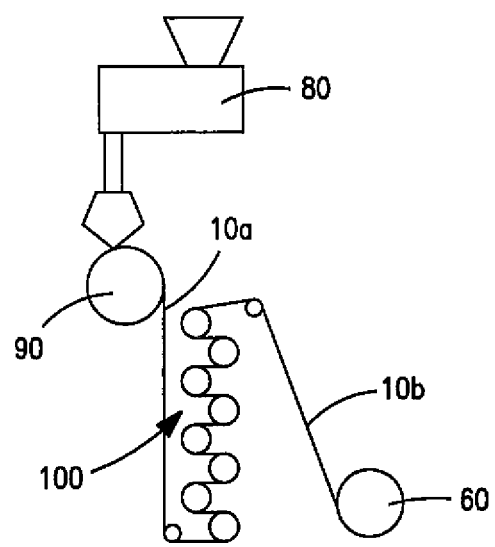
FIG. 1 is a schematic illustration of one embodiment of a method for forming a film in accordance with the present invention.

Repeat use of references characters in the present specification and drawings is intended to represent same or analogous features or elements of the invention.

DETAILED DESCRIPTION OF REPRESENTATIVE EMBODIMENTS

Definitions

As used herein, the terms "machine direction" or "MD" generally refers to the direction in which a material is produced. The term "cross-machine direction" or "CD" refers to the direction perpendicular to the machine direction. Dimensions measured in the cross-machine direction are referred to as "width" dimension, while dimensions measured in the machine direction are referred to as "length" dimensions.

As used herein, the term "elastomeric" and "elastic" and refers to a material that, upon application of a stretching force, is stretchable in at least one direction (such as the CD direction), and which upon release of the stretching force, contracts/returns to approximately its original dimension. For example, a stretched material may have a stretched length that is at least 50% greater than its relaxed unstretched length, and which will recover to within at least 50% of its stretched length upon release of the stretching force. A hypothetical example would be a one (1) inch sample of a material that is stretchable to at least 1.50 inches and which, upon release of the stretching force, will recover to a length of at least 1.25 inches. Desirably, the material contracts or recovers at least 50%, and even more desirably, at least 80% of the stretched length.

As used herein the terms "extensible" or "extensibility" generally refers to a material that stretches or extends in the direction of an applied force by at least about 50% of its relaxed length or width. An extensible material does not necessarily have recovery properties. For example, an elastomeric material is an extensible material having recovery properties. A film may be extensible, but not have recovery properties, and thus, be an extensible, non-elastic material.

As used herein, the term "percent stretch" refers to the degree to which a material stretches in a given direction when subjected to a certain force. In particular, percent stretch is determined by measuring the increase in length of the material in the stretched dimension, dividing that value by the original dimension of the material, and then multiplying by 100.

As used herein, the term "set" refers to retained elongation in a material sample following the elongation and recovery, i.e., after the material has been stretched and allowed to relax during a cycle test.

As used herein, the term "percent set" is the measure of the amount of the material stretched from its original length after being stretched and relaxed. The remaining strain after the removal of the applied stress is measured as the percent set.

Detailed Description

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention covers such modifications and variations as come within the scope of the appended claims and their equivalents.

Generally speaking, the present invention is directed to a film that contains a thermoplastic composition having a substantial portion of a renewable, natural starch polymer, and yet is elastic and exhibits good strength properties. Although starch is normally chemically incompatible with most elastomeric polymers due to their different polarities, the present inventors have discovered that phase separation may be minimized by selectively controlling certain aspects of the film, such as the nature of the elastomeric polymer and the starch polymer, and other film components, the relative amount of the film components, and the process for making the film.

Various embodiments of the present invention will now be described in more detail below.

I. Thermoplastic Composition

A. Elastomeric Polymer

Any of a variety of different elastomeric polymers may be employed in the film of the present invention, such as elastomeric polyesters, elastomeric polyurethanes, elastomeric polyamides, elastomeric copolymers, and so forth. In one embodiment, for example, an olefinic elastomer is employed that is a polyolefin capable of exhibiting a substantially regular structure ("semi-crystalline"). Such olefinic elastomers may be substantially amorphous in their undeformed state, but form crystalline domains upon stretching. The degree of crystallinity of the olefin polymer may be from about 3% to about 30%, in some embodiments from about 5% to about 25%, and in some embodiments, from about 5% and about 15%. Likewise, the olefinic elastomer may have a latent heat of fusion ($\Delta H_f$), which is another indicator of the degree of crystallinity, of from about 15 to about 75 Joules per gram ("J/g"), in some embodiments from about 20 to about 65 J/g, and in some embodiments, from 25 to about 50 J/g. The olefinic elastomer may also have a Vicat softening temperature of from about 10° C. to about 100° C., in some embodiments from about 20° C. to about 80° C., and in some embodiments, from about 30° C. to about 60° C. The olefinic elastomer may have a melting temperature of from about 20° C. to about 120° C., in some embodiments from about 35° C. to about 90° C., and in some embodiments, from about 40° C. to about 80° C. The latent heat of fusion ($\Delta H_f$) and melting temperature may be determined using differential scanning calorimetry ("DSC") in accordance with ASTM D-3417 as is well known to those skilled in the art. The Vicat softening temperature may be determined in accordance with ASTM D-1525.

Exemplary semi-crystalline olefinic elastomers include polyethylene, polypropylene, blends and copolymers thereof. In one particular embodiment, a polyethylene is employed that is a copolymer of ethylene and an α-olefin, such as a $C_3$-$C_{20}$ α-olefin or $C_3$-$C_{12}$ α-olefin. Suitable α-olefins may be linear or branched (e.g., one or more $C_1$-$C_3$ alkyl branches, or an aryl group). Specific examples include 1-butene; 3-methyl-1-butene; 3,3-dimethyl-1-butene; 1-pentene; 1-pentene with one or more methyl, ethyl or propyl substituents; 1-hexene with one or more methyl, ethyl or propyl substituents; 1-heptene with one or more methyl, ethyl or propyl substituents; 1-octene with one or more methyl, ethyl or propyl substituents; 1-nonene with one or more methyl, ethyl or propyl substituents; ethyl, methyl or dimethyl-substituted 1-decene; 1-dodecene; and styrene. Particularly desired α-olefin comonomers are 1-butene, 1-hexene and 1-octene. The ethylene content of such copolymers may be from about 60 mole % to about 99 mole %, in some embodiments from about 80 mole % to about 98.5 mole %, and in some embodiments, from about 87 mole % to about 97.5 mole %. The α-olefin content may likewise range from about 1 mole % to about 40 mole %, in some embodiments from about 1.5 mole % to about 15 mole %, and in some embodiments, from about 2.5 mole % to about 13 mole %. Propylene polymers may also be suitable for use as an olefinic elastomer. In one particular embodiment, the semi-crystalline propylene-based polymer includes a copolymer of propylene and an α-olefin, such as a $C_2$-$C_{20}$ α-olefin or $C_2$-$C_{12}$ α-olefin. Particularly desired α-olefin comonomers are ethylene, 1-butene, 1-hexene and 1-octene. The propylene content of such copolymers may be from about 60 mole % to about 99.5 wt. %, in some embodiments from about 80 mole % to about 99 mole %, and in some embodiments, from about 85 mole % to about 98 mole %. The α-olefin content may likewise range from about 0.5 mole % to about 40 mole %, in some embodiments from about 1 mole % to about 20 mole %, and in some embodiments, from about 2 mole % to about 15 mole %.

Any of a variety of known techniques may generally be employed to form the olefinic elastomers. For instance, olefin polymers may be formed using a free radical or a coordination catalyst (e.g., Ziegler-Natta). Preferably, the olefin polymer is formed from a single-site coordination catalyst, such as a metallocene catalyst. Such a catalyst system produces ethylene copolymers in which the comonomer is randomly distributed within a molecular chain and uniformly distributed across the different molecular weight fractions. Metallocene-catalyzed polyolefins are described, for instance, in U.S. Pat. No. 5,571,619 to McAlpin et al.; U.S. Pat. No. 5,322,728 to Davis et al.; U.S. Pat. No. 5,472,775 to Obiieski et al.; U.S. Pat. No. 5,272,236 to Lai et al.; and U.S. Pat. No. 6,090,325 to Wheat, et al., which are incorporated herein in their entirety by reference thereto for all purposes. Examples of metallocene catalysts include bis(n-butylcyclopentadienyl)titanium dichloride, bis(n-butylcyclopentadienyl)zirconium dichloride, bis(cyclopentadienyl)scandium chloride, bis(indenyl)zirconium dichloride, bis(methylcyclopentadienyl)titanium dichloride, bis(methylcyclopentadienyl)zirconium dichloride, cobaltocene, cyclopentadienyltitanium trichloride, ferrocene, hafnocene dichloride, isopropyl(cyclopentadienyl,-1-flourenyl)zirconium dichloride, molybdocene dichloride, nickelocene, niobocene dichloride, ruthenocene, titanocene dichloride, zirconocene chloride hydride, zirconocene dichloride, and so forth. Polymers made using metallocene catalysts typically have a narrow molecular weight range. For instance, metallocene-catalyzed polymers may have polydispersity numbers ($M_w/M_n$) of below 4, controlled short chain branching distribution, and controlled isotacticity.

The density of such α-olefin copolymers is a function of both the length and amount of the α-olefin. That is, the greater the length of the α-olefin and the greater the amount of α-olefin present, the lower the density of the copolymer. Although not necessarily required, substantially linear elastomers are particularly desirable in that the content of α-olefin short chain branching content is such that the copolymer exhibits both plastic and elastomeric characteristics. Because polymerization with α-olefin comonomers decreases crystallinity and density, the resulting elastomer normally has a density lower than that of polyethylene thermoplastic polymers (e.g., LLDPE), but approaching and/or overlapping that of other elastomers. For example, the density of the olefinic elastomer may be about 0.91 grams per cubic centimeter (g/cm$^3$) or less, in some embodiments from about 0.85 to about 0.89 g/cm$^3$, and in some embodiments, from about 0.85 g/cm$^3$ to about 0.88 g/cm$^3$.

Preferred ethylene elastomers for use in the present invention are ethylene-based copolymer plastomers available under the EXACT™ from ExxonMobil Chemical Company of Houston, Tex. Other suitable polyethylene plastomers are available under the designation ENGAGE™ and AFFINITY™ from Dow Chemical Company of Midland, Mich. Still other suitable ethylene polymers are available from The Dow Chemical Company under the designations DOWLEX™ (LLDPE) and ATTANE™ (ULDPE). Such ethylene polymers are described in U.S. Pat. No. 4,937,299 to Ewen et al.; U.S. Pat. No. 5,218,071 to Tsutsui at al.; U.S. Pat. No. 5,272,236 to Lai, et al.; and U.S. Pat. No. 5,278,272 to Lai, et al., which are incorporated herein in their entirety by reference thereto for all purposes. Suitable propylene polymers are commercially available under the designations VISTAMAXX™ from ExxonMobil Chemical Co. of Houston, Tex.; FINA™ (e.g., 8573) from Atofina Chemicals of Feluy, Belgium; TAFMER™ available from Mitsui Petrochemical Industries; and VERSIFY™ available from Dow Chemical Co. of Midland, Mich. Other examples of suitable propylene polymers are described in U.S. Pat. No. 6,500,563 to Datta, et al.; U.S. Pat. No. 5,539,056 to Yang, et al.; and U.S. Pat. No. 5,596,052 to Resconi, et al., which are incorporated herein in their entirety by reference thereto for all purposes.

The melt flow index (MI) of the olefinic elastomers may generally vary, but is typically in the range of about 0.1 grams per 10 minutes to about 100 grams per 10 minutes, in some embodiments from about 0.5 grams per 10 minutes to about 30 grams per 10 minutes, and in some embodiments, about 1 to about 10 grams per 10 minutes, determined at 190° C. The melt flow index is the weight of the polymer (in grams) that may be forced through an extrusion rheometer orifice (0.0825-inch diameter) when subjected to a force of 2.16 kilograms in 10 minutes at 190° C., and may be determined in accordance with ASTM Test Method D1238-E.

Of course, other olefinic elastomers may also be employed in the present invention. In one embodiment, for example, the thermoplastic elastomer may be a styrene-olefin block copolymer, such as styrene-(ethylene-butylene), styrene-(ethylene-propylene), styrene-(ethylene-butylene)-styrene, styrene-(ethylene-propylene)-styrene, styrene-(ethylene-butylene)-styrene-(ethylene-butylene), styrene-(ethylene-propylene)-styrene-(ethylene-propylene), and styrene-ethylene-(ethylene-propylene)-styrene. Such polymers may be formed by selective hydrogenation of styrene-diene block copolymers, such as described in U.S. Pat. Nos. 4,663,220, 4,323,534, 4,834,738, 5,093,422 and 5,304,599, which are hereby incorporated in their entirety by reference thereto for all purposes. Particularly suitable thermoplastic elastomers are available from Kraton Polymers LLC of Houston, Tex. under the trade name KRATON®. Other commercially available block copolymers include the S-EP-S elastomeric copolymers available from Kuraray Company, Ltd. of Okayama, Japan, under the trade designation SEPTON®. Also suitable are polymers composed of an A-B-A-B tetrablock copolymer, such as discussed in U.S. Pat. No. 5,332,613 to Taylor, et al., which is incorporated herein in its entirety by reference thereto for all purposes. An example of such a tetrablock copolymer is a styrene-poly(ethylene-propylene)-styrene-poly(ethylene-propylene) ("S-EP-S-EP") block copolymer.

As stated, thermoplastic polyurethanes may also be employed in the present invention, either alone or in combination with another type of elastomer (e.g., olefinic elastomer). Thermoplastic polyurethanes are generally synthesized from a polyol, organic diisocyanate, and optionally a chain extender. The synthesis of such melt-processable polyurethane elastomers may proceed either stepwise (e.g., prepolymer dispensing process) or by simultaneous reaction of all components in a single stage (e.g., one-shot dispensing process) as is known in the art and described in more detail in U.S. Pat. No. 3,963,656 to Meisert, et al.; U.S. Pat. No. 5,605,961 to Lee, et al.; U.S. Pat. No. 6,008,276 to Kalbe, et al.; U.S. Pat. No. 6,417,313 to Kirchmeyer, et al.; and U.S. Pat. No. 7,045,650 to Lawrey, et al., as well as U.S. Patent Application Publication Nos. 2006/0135728 to Peerlinds, et al. and 2007/0049719 to Brauer, et al., all of which are incorporated herein in their entirety by reference thereto for all purposes.

A polyol is generally any high molecular weight product having an active hydrogen component that may be reacted and includes materials having an average of about two or more hydroxyl groups per molecule. Long-chain polyols may be used that include higher polymeric polyols, such as polyester polyols and polyether polyols, as well as other acceptable "polyol" reactants, which have an active hydrogen component such as polyester polyols, polyhydroxy polyester amides, hydroxyl containing polycaprolactones, hydroxy-containing acrylic interpolymers, hydroxy-containing epoxies, and hydrophobic polyalkylene ether polyols. Typically, the polyol is substantially linear and has two to three, and more preferably two hydroxyl groups, and a number average molecular weight of from about 450 to about 10,000, in some embodiments from about 450 to about 6000, and in some embodiments from about 600 to about 4500. Suitable polyether diols may be produced by, for example, reacting one or more alkylene oxides having 2 to 4 carbon atoms in the alkylene residue with a starter molecule that contains two or more active hydrogen atoms in bound form. Exemplary alkylene oxides include ethylene oxide, 1,2-propylene oxide, epichlorohydrin and 1,2-butylene oxide and 2,3-butylene oxide. Exemplary starter molecules include water; aminoalcohols, such as N-alkyl-diethanolamines (e.g., N-methyl-diethanolamine); and diols, such as ethylene glycol, 1,3-propylene glycol, 1,4-butanediol and 1,6-hexanediol. Suitable polyester diols may be produced from dicarboxylic acids (or derivatives thereof) having 2 to 12 carbon atoms, preferably 4 to 6 carbon atoms, and polyhydric alcohols. Exemplary dicarboxylic acids include aliphatic dicarboxylic acids, such as succinic acid, glutaric acid, adipic acid, suberic acid, azelaic acid and sebacic acid; aromatic dicarboxylic acids, such as phthalic acid, isophthalic acid and terephthalic acid; as well as derivatives of such acids, such as carboxylic acid diesters having 1 to 4 carbon atoms in the alcohol residue, carboxylic anhydrides or carboxylic acid chlorides. Examples of suitable polyhydric alcohols include glycols with 2 to 10, preferably 2 to 6 carbon atoms, such as ethylene glycol, diethylene glycol, 1,4-butanediol, 1,5-pentanediol, 1,6-hexanediol, 1,10-decanediol, 2,2-dimethyl-1,3-propanediol, 1,3-propanediol, and dipropylene glycol. Esters of carbonic acid with the stated diols are also suitable, and particularly, those having 4 to 6 carbon atoms, such as 1,4-butanediol or 1,6-hexanediol; condensation products of ω-hydroxycarboxylic acids, such as ω-hydroxycaproic acid or polymerisation products of lactones (e.g., optionally substituted ω-caprolactones). Preferred polyester diols include ethanediol polyadipates, 1,4-butanediol polyadipates, ethanediol/1,4-butanediol polyadipates, 1,6-hexanediol/neopentyl glycol polyadipates, 1,6-hexanediol/1,4-butanediol polyadipates and polycaproplactones.

The organic diisocyanates may include aliphatic diisocyanates, such as ethylene diisocyanate, 1,4-tetramethylene diisocyanate, 1,12-dodecane diisocyanate, 1,6-hexamethylene diisocyanate, mixtures thereof, etc.; cycloaliphatic diisocyanates, such as isophorone diisocyanate, 1,4-cyclohexane diisocyanate, 1-methyl-2,4-cyclohexane diisocyanate, 1-methyl-2,6-cyclohexane diisocyanate, 4,4'-, 2,4'- or 2,2'-dicyclohexylmethane diisocyanate, mixtures thereof, etc.; and/or aromatic diisocyanates, such as 2,4- or 2,6-toluene diisocyanate, 4,4'-diphenylmethane diisocyanate, 2,4'-diphenylmethane diisocyanate, 2,2'-diphenylmethane diisocyanate, naphthylene-1,5-diisocyanate, xylylene diisocyanate, methylene diphenyl isocyanate ("MDI"), hexamethylene diisocyanate ("HMDI"), mixtures thereof, etc.

The chain extenders typically have a number average molecular weight of from about 60 to about 400 and contains amino, thiol, carboxyl, and/or hydroxyl functional groups. The preferred chain extenders are those having two to three, and more preferably two, hydroxyl groups. As set forth above, one or more compounds selected from the aliphatic diols that contain from 2 to 14 carbon atoms may be used as the chain extender. Such compounds include, for example, ethanediol, 1,2-propanediol, 1,3-propanediol, 1,4-butanediol, 2,3-butanediol, 1,5-pentanediol, 1,6-hexanediol, diethylene glycol, dipropylene glycol, 1,4-cyclohexanediol, 1,4-dimethanolcyclohexane and neopentyl glycol. Diesters of terephthalic acid with glycols having 2 to 4 carbon atoms may also be employed. Some examples of such compounds include terephthalic acid bis-ethylene glycol and terephthalic acid bis-1,4-butanediol, hydroxyalkylene ethers of hydroquinone (e.g., 1-4-di(β-hydroxyethyl)hydroquinone), ethoxylated bisphenols (e.g., 1,4-di(β-hydroxyethyl)bisphenol A), (cyclo)aliphatic diamines (e.g., isophoronediamine, ethylendiamine, 1,2-propylenediamine, 1,3-propylenediamine, N-methyl-1,3-propylenediamine, and N,N'-dimethylethylenediamine), and aromatic diamines (e.g., 2,4-toluenediamine, 2,6-toluenediamine, 3,5-diethyl-2,4-toluenediamine and 3,5-diethyl-2,6-toluenediamine, and primary mono-, di-, tri- or tetraalkyl-substituted 4,4'-diaminodiphenylmethanes).

In addition to those noted above, other components may also be employed to form the thermoplastic polyurethane. Catalysts, for instance, may be employed to facilitate formation of the polyurethane. Suitable catalysts include, for instance, tertiary amines, such as triethylamine, dimethylcyclohexyl-amine, N-methylmorpholine, N,N'-dimethylpiperazine, 2-(dimethylaminoethoxy)-ethanol, diazabicyclo [2.2.2]octane, etc. as well as metal compounds, such as titanic acid esters, tin diacetate, tin dioctoate, tin dilaurate or the dialkyltin salts of aliphatic carboxylic acids such as dibutyltin diacetate or dibutyltin dilaurate or other similar compounds. Still other suitable additives that may be employed include light stablizers (e.g., hindered amines), chain terminators, slip agents and mold release agents (e.g., fatty acid esters, the metal soaps thereof, fatty acid amides, fatty acid ester amides and silicone compounds), plasticizers, antiblocking agents, inhibitors, stabilizers against hydrolysis, heat and discoloration, dyes, pigments, inorganic and/or organic fillers, fungistatically and bacteriostatically active substances, fillers, etc.

The thermoplastic polyurethane typically has a melting point of from about 75° C. to about 250° C., in some embodiments from about 100° C. to about 240° C., and in some embodiments, from about 120° C. to about 220° C. The glass transition temperature ("$T_g$") of the thermoplastic polyurethane may be relatively low, such as from about −150° C. to about 0° C., in some embodiments from about −100° C. to about −10° C., and in some embodiments, from about −85° C. to about −20° C. The melting temperature and glass transition temperature may be determined using differential scanning calorimetry ("DSC") in accordance with ASTM D-3417. Examples of such thermoplastic polyurethanes are available under the designation DESMOPAN™ from Bayer Material-Science and under the designation ESTANE™ from Lubrizol. DESMOPAN™ DP 9370A, for instance, is an aromatic polyether-based polyurethane formed from poly(tetramethylene ether glycol) and 4,4-methylenebis-(phenylisocyanate) ("MDI") and has a glass transition temperature of about −70° C. and a melting temperature of from about 188° C. to about 199° C. ESTANE™ 58245 is likewise an aromatic polyether-based polyurethane having a glass transition temperature of about −37° C. and a melting temperature of from about 135° C. to about 159° C.

B. Starch Polymer

Although starch polymers are produced in many plants, typical sources includes seeds of cereal grains, such as corn, waxy corn, wheat, sorghum, rice, and waxy rice; tubers, such as potatoes; roots, such as tapioca (i.e., cassava and manioc), sweet potato, and arrowroot; and the pith of the sago palm. The starch polymer may contain different weight percentages of amylose and amylopectin, different polymer molecular weights, etc. High amylose starches contain greater than about 50% by weight amylose and low amylose starches contain less than about 50% by weight amylose. Although not required, low amylose starches having an amylose content of from about 10% to about 40% by weight, and in some embodiments, from about 15% to about 35% by weight, are particularly suitable for use in the present invention. Examples of such low amylose starches include corn starch and potato starch, both of which have an amylose content of approximately 20% by weight. Particularly suitable low amylase starches are those having a number average molecular weight ("Mn") ranging from about 50,000 to about 1,000,000 grams per mole, in some embodiments from about 75,000 to about 800,000 grams per mole, and in some embodiments, from about 100,000 to about 600,000 grams per mole, and/or a weight average molecular weight ("Mw") ranging from about 5,000,000 to about 25,000,000 grams per mole, in some embodiments from about 5,500,000 to about 15,000,000 grams per mole, and in some embodiments, from about 6,000,000 to about 12,000,000 grams per mole. The ratio of the weight average molecular weight to the number average molecular weight ("Mw/Mn"), i.e., the "polydispersity index", is also relatively high.

For example, the polydispersity index may range from about 10 to about 100, and in some embodiments, from about 20 to about 80. The weight and number average molecular weights may be determined by methods known to those skilled in the art.

Although native starches are typically desired because they are more natural, chemically modified starches may also be employed in the present invention. Chemically modified starches may be obtained through typical processes known in the art (e.g., esterification, etherification, oxidation, acid hydrolysis, enzymatic hydrolysis, etc.). Starch ethers and/or esters may be particularly desirable, such as hydroxyalkyl starches, carboxymethyl starches, etc. The hydroxyalkyl group of hydroxyalkyl starches may contain, for instance, 2 to 10 carbon atoms, in some embodiments from 2 to 6 carbon atoms, and in some embodiments, from 2 to 4 carbon atoms. Representative hydroxyalkyl starches such as hydroxyethyl starch, hydroxypropyl starch, hydroxybutyl starch, and derivatives thereof. Starch esters, for instance, may be prepared using a wide variety of anhydrides (e.g., acetic, propionic, butyric, and so forth), organic acids, acid chlorides, or other esterification reagents. The degree of esterification may vary as desired, such as from 1 to 3 ester groups per glucosidic unit of the starch.

Regardless of the particular polymers employed, the relative amount of starch polymers employed in the film is generally high enough to achieve a certain degree of renewability, but not so high so that good elongation properties are not achieved. In this regard, the starch polymers typically constitute from about 1 wt. % to about 30 wt. %, in some embodiments from about 2 wt. % to about 25 wt. %, and in some embodiments, from about 5 wt. % to about 20 wt % of the polymer content of the film. Within these ranges, the present inventors have discovered that excellent elongation properties may be achieved while still employing a relatively high amount of the renewable component. Furthermore, while the percentage of the entire film constituted by the starch polymers may vary depending on the other ingredients employed (e.g., fillers), they typically constitute from about 0.5 wt. % to about 50 wt. %, in some embodiments from about 1 wt. % to about 40 wt. %, and in some embodiments, from about 5 wt. % to about 25 wt. % of the entire film. It should be understood that the weight of starch referenced herein includes any bound water that naturally occurs in the starch before mixing it with other components to form the thermoplastic starch. Starches, for instance, typically have a bound water content of about 5% to 16% by weight of the starch.

To achieve the desired balance between renewability and elongation, the weight ratio of elastomeric polymers to the starch polymers is also typically from about 1 to about 10, in some embodiments from about 2 to about 8, and in some embodiments, from about 3 to about 6. For instance, elastomeric polymers may constitute from about 30 wt. % to about 95 wt. %, in some embodiments from about 40 wt. % to about 90 wt. %, and in some embodiments, from about 50 wt. % to about 80 wt % of the polymer content of the film. Furthermore, while the percentage of the entire film constituted by the elastomeric polymers may vary depending on the other ingredients employed (e.g., fillers), they typically constitute from about 10 wt. % to about 90 wt. %, in some embodiments from about 20 wt. % to about 80 wt. %, and in some embodiments, from about 40 wt. % to about 75 wt % of the entire film.

C. Plasticizer

A plasticizer is also employed in the film to help render the starch melt-processible. Starches, for instance, normally exist in the form of granules that have a coating or outer membrane that encapsulates the more water-soluble amylose and amylopectin chains within the interior of the granule. When heated, plasticizers may soften and penetrate the outer membrane and cause the inner starch chains to absorb water and swell. This swelling will, at some point, cause the outer shell to rupture and result in an irreversible destructurization of the starch granule. Once destructurized, the starch polymer chains containing amylose and amylopectin polymers, which are initially compressed within the granules, will stretch out and form a generally disordered intermingling of polymer chains. Upon resolidification, however, the chains may reorient themselves to form crystalline or amorphous solids having varying strengths depending on the orientation of the starch polymer chains. Because the starch is thus capable of melting and resolidifying at certain temperatures, it is generally considered a "thermoplastic starch."

Suitable plasticizers may include, for instance, polyhydric alcohol plasticizers, such as sugars (e.g., glucose, sucrose, fructose, raffinose, maltodextrose, galactose, xylose, maltose, lactose, mannose, and erythrose), sugar alcohols (e.g., erythritol, xylitol, malitol, mannitol, and sorbitol), polyols (e.g., ethylene glycol, glycerol, propylene glycol, dipropylene glycol, butylene glycol, and hexane triol), etc. Also suitable are hydrogen bond forming organic compounds which do not have hydroxyl group, including urea and urea derivatives; anhydrides of sugar alcohols such as sorbitan; animal proteins such as gelatin; vegetable proteins such as sunflower protein, soybean proteins, cotton seed proteins; and mixtures thereof. Other suitable plasticizers may include phthalate esters, dimethyl and diethylsuccinate and related esters, glycerol triacetate, glycerol mono and diacetates, glycerol mono, di, and tripropionates, butanoates, stearates, lactic acid esters, citric acid esters, adipic acid esters, stearic acid esters, oleic acid esters, and other acid esters. Aliphatic acids may also be used, such as copolymers of ethylene and acrylic acid, polyethylene grafted with maleic acid, polybutadiene-co-acrylic acid, polybutadiene-co-maleic acid, polypropylene-co-acrylic acid, polypropylene-co-maleic acid, and other hydrocarbon based acids. A low molecular weight plasticizer is preferred, such as less than about 20,000 g/mol, preferably less than about 5,000 g/mol and more preferably less than about 1,000 g/mol.

If desired, the plasticizer may be pre-blended with the starch polymer to form a "thermoplastic starch." In such embodiments, the starch polymers may constitute from about 40 wt. % to about 98 wt. %, in some embodiments from about 50 wt. % to about 95 wt. %, and in some embodiments, from about 60 wt. % to about 90 wt. % of the thermoplastic starch. Likewise, the plasticizer typically constitutes from about 2 wt. % to about 60 wt. %, in some embodiments from about 5 wt. % to about 50 wt. %, and in some embodiments, from about 10 wt. % to about 40 wt. % of the thermoplastic starch. Regardless of whether it is pre-blended with the starch polymer, or simply combined therewith during formation of the film, the plasticizers typically constitute from about 0.1 wt. % to about 30 wt. %, in some embodiments from about 0.5 wt. % to about 20 wt. %, and in some embodiments, from about 1 wt. % to about 10 wt % of the film.

D. Other Components

In addition to those noted above, still other additives may also be incorporated into the thermoplastic starch or in the entire film. For example, dispersion aids may be employed to help create a uniform dispersion of the starch/plasticizer/elastomeric polymer and retard or prevent separation into constituent phases. When employed, the dispersion aid(s) may constitute from about 0.01 wt. % to about 10 wt. %, in some embodiments from about 0.05 wt. % to about 5 wt. %, and in some embodiments, from about 0.1 wt. % to about 4 wt. % of the film.

Although any dispersion aid may generally be employed in the present invention, surfactants having a certain hydrophilic/lipophilic balance may improve the long-term stability of the composition. As is known in the art, the relative hydrophilicity or lipophilicity of an emulsifier can be characterized by the hydrophilic/lipophilic balance ("HLB") scale, which measures the balance between the hydrophilic and lipophilic solution tendencies of a compound. The HLB scale ranges from 0.5 to approximately 20, with the lower numbers representing highly lipophilic tendencies and the higher numbers representing highly hydrophilic tendencies. In some embodiments of the present invention, the HLB value of the surfactants is from about 1 to about 15, in some embodiments from about 1 to about 12 and in some embodiments, from about 2 to about 10. If desired, two or more surfactants may be employed that have HLB values either below or above the desired value, but together have an average HLB value within the desired range.

One particularly suitable class of surfactants for use in the present invention are nonionic surfactants, which typically have a hydrophobic base (e.g., long chain alkyl group or an alkylated aryl group) and a hydrophilic chain (e.g., chain contaiing ethoxy and/or propoxy moieties). For instance, some suitable nonionic surfactants that may be used include, but are not limited to, ethoxylated alkylphenols, ethoxylated and propoxylated fatty alcohols, polyethylene glycol ethers of methyl glucose, polyethylene glycol ethers of sorbitol, ethylene oxide-propylene oxide block copolymers, ethoxylated esters of fatty ($C_8$-$C_{18}$) acids, condensation products of ethylene oxide with long chain amines or amides, condensation products of ethylene oxide with alcohols, fatty acid esters, monoglyceride or diglycerides of long chain alcohols, and mixtures thereof. In one particular embodiment, the nonionic surfactant may be a fatty acid ester, such as a sucrose fatty acid ester, glycerol fatty acid ester, propylene glycol fatty acid ester, sorbitan fatty acid ester, pentaerythritol fatty acid ester, sorbitol fatty acid ester, and so forth. The fatty acid used to form such esters may be saturated or unsaturated, substituted or unsubstituted, and may contain from 6 to 22 carbon atoms, in some embodiments from 8 to 18 carbon atoms, and in some embodiments, from 12 to 14 carbon atoms. In one particular embodiment, mono- and di-glycerides of fatty acids may be employed in the present invention.

Other components may also be incorporated into the thermoplastic composition used to form the film. For example, the film may contain one or more synthetic biodegradable polyesters. The term "biodegradable" generally refers to a material that degrades from the action of naturally occurring microorganisms, such as bacteria, fungi, and algae; environmental heat; moisture; or other environmental factors, such as determined according to ASTM Test Method 5338.92. Examples of suitable synthetic biodegradable polyesters include aliphatic polyesters, such as polycaprolactone, polyesteramides, modified polyethylene terephthalate, polylactic acid (PLA) and its copolymers, terpolymers based on polylactic acid, polyglycolic acid, polyalkylene carbonates (such as polyethylene carbonate), polyhydroxyalkanoates (PHA), poly-3-hydroxybutyrate (PHB), poly-3-hydroxyvalerate (PHV), poly-3-hydroxybutyrate-co-4-hydroxybutyrate, poly-3-hydroxybutyrate-co-3-hydroxyvalerate copolymers (PHBV), poly-3-hydroxybutyrate-co-3-hydroxyhexanoate, poly-3-hydroxybutyrate-co-3-hydroxyoctanoate, poly-3-hydroxybutyrate-co-3-hydroxydecanoate, poly-3-hydroxybutyrate-co-3-hydroxyoctadecanoate, and succinate-based aliphatic polymers (e.g., polybutylene succinate, polybutylene succinate adipate, polyethylene succinate, etc.); aromatic polyesters and modified aromatic polyesters; and aliphatic-aromatic copolyesters. For example, the biodegradable polyester may be an aliphatic-aromatic copolyester having the following structure:

about 5 wt % to about 60 wt. %, and in some embodiments, from about 10 wt. % to about 50 wt % of the entire film.

In addition to the components noted above, other additives may also be incorporated into the film of the present invention, such as slip additives, melt stabilizers, processing stabilizers, heat stabilizers, light stabilizers, antioxidants, heat aging stabilizers, whitening agents, bonding agents, fillers, etc. Fillers, for example, are particulates or other forms of material that may be added to the film polymer extrusion blend and that will not chemically interfere with the extruded film, but which may be uniformly dispersed throughout the film. Fillers may serve a variety of purposes, including enhancing film opacity and/or breathability (i.e., vapor-permeable and substantially liquid-impermeable). Further, hindered phenols are commonly used as an antioxidant in the production of films. Some suitable hindered phenols include those available from Ciba Specialty Chemicals under the trade name "Irganox®", such as Irganox® 1076, 1010, or E 201. Moreover, bonding agents may also be added to the film to facilitate bonding of the film to additional materials (e.g., nonwoven webs). Examples of such bonding agents include hydrogenated hydrocarbon resins. Other suitable bonding agents are described in U.S. Pat. No. 4,789,699 to Kieffer et al. and U.S. Pat. No. 5,695,868 to McCormack, which are incorporated herein in their entirety by reference thereto for all purposes.

II. Film Construction

The film of the present invention may be mono- or multi-layered. Multilayer films may be prepared by co-extrusion of the layers, extrusion coating, or by any conventional layering

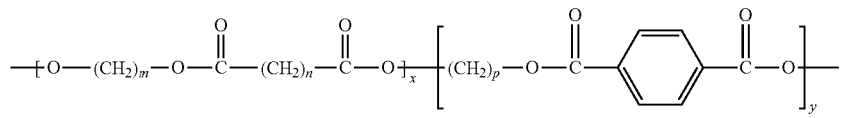

wherein, m is an integer from 2 to 10, in some embodiments from 2 to 4, and in one embodiment, 4;

n is an integer from 0 to 18, in some embodiments from 2 to 4, and in one embodiment, 4;

p is an integer from 2 to 10, in some embodiments from 2 to 4, and in one embodiment, 4;

x is an integer greater than 1; and y is an integer greater than 1. One example of such a copolyester is polybutylene adipate terephthalate, which is commercially available under the designation ECOFLEX® F BX 7011 from BASF Corp, Another example of a suitable copolyester containing an aromatic terephtalic acid monomer constituent is available under the designation ENPOL™ 8060M from IRE Chemicals (South Korea). Other suitable aliphatic-aromatic copolyesters may be described in U.S. Pat. Nos. 5,292,783; 5,446,079; 5,559,171; 5,580,911; 5,599,858; 5,817,721; 5,900,322; and 6,258,924, which are incorporated herein in their entirety by reference thereto for all purposes.

When employed, the synthetic biodegradable polyesters may constitute from about 5 wt. % to about 60 wt. %, in some embodiments from about 10 wt. % to about 50 wt. %, and in some embodiments, from about 15 wt. % to about 40 wt. % of the polymer content of the film. Furthermore, while the percentage of the entire film constituted by the biodegradable polyesters may vary depending on the other ingredients employed (e.g., fillers), they may generally constitute from about 1 wt. % to about 70 wt. %, in some embodiments from process. Such multilayer films normally contain at least one base layer and at least one skin layer, but may contain any number of layers desired. For example, the multilayer film may be formed from a base layer and one or more skin layers, wherein the base layer is formed from a blend of the elastomeric polymer and the thermoplastic starch polymer. In most embodiments, the skin layer(s) are also formed from the blend as described above. It should be understood, however, that other polymers may also be employed in the skin layer(s).

Any known technique may be used to form a film from the compounded material, including blowing, casting, flat die extruding, etc. In one particular embodiment, the film may be formed by a blown process in which a gas (e.g., air) is used to expand a bubble of the extruded polymer blend through an annular die.

The bubble is then collapsed and collected in flat film form. Processes for producing blown films are described, for instance, in U.S. Pat. No. 3,354,506 to Raley; U.S. Pat. No. 3,650,649 to Schippers; and U.S. Pat. No. 3,801,429 to Schrenk et al., as well as U.S. Patent Application Publication Nos. 2005/0245162 to McCormack, et al. and 2003/0068951 to Boggs, et al., all of which are incorporated herein in their entirety by reference thereto for all purposes. In yet another embodiment, however, the film is formed using a casting technique.

Referring to FIG. 1, for instance, one embodiment of a method for forming a cast film is shown. The raw materials (e.g., thermoplastic starch polymer, elastomeric polymer, etc.) may be supplied to a melt blending device, either separately or as a blend. In one embodiment, for example, the components are separately supplied to a melt blending device where they are dispersively blended in a manner such as described above. For example, an extruder may be employed that includes feeding and venting ports. In one embodiment, the elastomeric polymer may be fed to a feeding port of the twin-screw extruder and melted. Thereafter, the thermoplastic starch polymer may be fed into the polymer melt. Regardless, the materials are blended under high shear/pressure and heat to ensure sufficient mixing. For example, melt blending may occur at a temperature of from about 75° C. to about 400° C., in some embodiments, from about 80° C. to about 300° C., and in some embodiments, from about 90° C. to about 250° C. Likewise, the apparent shear rate during melt blending may range from about 100 seconds$^{-1}$ to about 10,000 seconds$^{-1}$, in some embodiments from about 500 seconds$^{-1}$ to about 5000 seconds$^{-1}$, and in some embodiments, from about 800 seconds$^{-1}$ to about 1200 seconds$^{-1}$. The apparent shear rate is equal to $4Q/\pi R^3$, where Q is the volumetric flow rate ("m$^3$/s") of the polymer melt and R is the radius ("m") of the capillary (e.g., extruder die) through which the melted polymer flows.

Thereafter, the extruded material may be immediately chilled and cut into pellet form. In the particular embodiment of FIG. 1, the compounded material (not shown) is then supplied to an extrusion apparatus 80 and cast onto a casting roll 90 to form a single-layered precursor film 10*a*. If a multilayered film is to be produced, the multiple layers are co-extruded together onto the casting roll 90. The casting roll 90 may optionally be provided with embossing elements to impart a pattern to the film. Typically, the casting roll 90 is kept at temperature sufficient to solidify and quench the sheet 10*a* as it is formed, such as from about 20 to 60° C. If desired, a vacuum box may be positioned adjacent to the casting roll 90 to help keep the precursor film 10*a* close to the surface of the roll 90. Additionally, air knives or electrostatic pinners may help force the precursor film 10*a* against the surface of the casting roll 90 as it moves around a spinning roll. An air knife is a device known in the art that focuses a stream of air at a very high flow rate to pin the edges of the film.

Once cast, the film 10*a* may then be optionally oriented in one or more directions to further improve film uniformity and reduce thickness. Orientation may also form micropores in a film containing a filler, thus providing breathability to the film. For example, the film may be immediately reheated to a temperature below the melting point of one or more polymers in the film, but high enough to enable the composition to be drawn or stretched. In the case of sequential orientation, the "softened" film is drawn by rolls rotating at different speeds of rotation such that the sheet is stretched to the desired draw ratio in the longitudinal direction (machine direction). This "uniaxially" oriented film may then be laminated to a fibrous web. In addition, the uniaxially oriented film may also be oriented in the cross-machine direction to form a "biaxially oriented" film. For example, the film may be clamped at its lateral edges by chain clips and conveyed into a tenter oven. In the tenter oven, the film may be reheated and drawn in the cross-machine direction to the desired draw ratio by chain clips diverged in their forward travel.

Referring again to FIG. 1, for instance, one method for forming a uniaxially oriented film is shown. As illustrated, the precursor film 10*a* is directed to a film-orientation unit 100 or machine direction orienter ("MDO"), such as commercially available from Marshall and Willams, Co. of Providence, R.I. The MDO has a plurality of stretching rolls (such as from 5 to 8) which progressively stretch and thin the film in the machine direction, which is the direction of travel of the film through the process as shown in FIG. 1. While the MDO 100 is illustrated with eight rolls, it should be understood that the number of rolls may be higher or lower, depending on the level of stretch that is desired and the degrees of stretching between each roll. The film may be stretched in either single or multiple discrete stretching operations. It should be noted that some of the rolls in an MDO apparatus may not be operating at progressively higher speeds. If desired, some of the rolls of the MDO 100 may act as preheat rolls. If present, these first few rolls heat the film 10*a* above room temperature (e.g., to 125° F.). The progressively faster speeds of adjacent rolls in the MDO act to stretch the film 10*a*. The rate at which the stretch rolls rotate determines the amount of stretch in the film and final film weight.

The resulting film 10*b* may then be wound and stored on a take-up roll 60. While not shown here, various additional potential processing and/or finishing steps known in the art, such as slitting, treating, aperturing, printing graphics, or lamination of the film with other layers (e.g., nonwoven web materials), may be performed without departing from the spirit and scope of the invention.

The thickness of the resulting elastic film may generally vary depending upon the desired use. In most embodiments of the present invention, however, the elastic film has a thickness of about 50 micrometers or less, in some embodiments from about 1 to about 100 micrometers, in some embodiments from about 5 to about 75 micrometers, and in some embodiments, from about 10 to about 60 micrometers.

Despite having such a small thickness, the film of the present invention is nevertheless able to retain good dry mechanical properties during use. One parameter that is indicative of the relative dry strength of the film is the ultimate tensile strength, which is equal to the peak stress obtained in a stress-strain curve. Desirably, the film of the present invention exhibits an ultimate tensile strength in the machine direction ("MD") and/or cross-machine direction ("CD") of from about 10 to about 80 Megapascals (MPa), in some embodiments from about 15 to about 60 MPa, and in some embodiments, from about 20 to about 50 MPa. Although possessing good strength, it is also desirable that the film is not too stiff. One parameter that is indicative of the relative stiffness of the film (when dry) is Young's modulus of elasticity, which is equal to the ratio of the tensile stress to the tensile strain and is determined from the slope of a stress-strain curve. For example, the film typically exhibits a Young's modulus in the machine direction ("MD") and/or cross-machine direction ("CD") of from about 1 to about 100 Megapascals ("MPa"), in some embodiments from about 2 to about 50 MPa, and in some embodiments, from about 5 to about 30 MPa.

The film is also generally extensible in that it possesses an elongation in the machine and/or cross-machine direction of about 250% or more, in some embodiments about 400% or more, in some embodiments from about 500% to about 2500%, and in some embodiments, from about 700% to about 2000%. Besides being extensible, the film is also generally elastic in that is capable of recovering at least about 50% of its stretched length upon release of the stretching force. The elasticity of the film may be characterized by its "percent set", which is typically about 30% or less, in some embodiments from about 1% to about 30%, and in some embodiments, from about 2% to about 10%.

Depending on the intended application, the elastic film of the present invention may also be generally liquid and vapor-impermeable or generally liquid impermeable, yet vapor-permeable (i.e., "breathable"). Breathable films, for example, are often used in absorbent articles (e.g., outer cover) in which it is desired to allow moisture to escape from the absorbent core through the film.

Similarly, bandages or wound dressings often employ breathable films that allow the release of moisture from the skin at the wound site. Breathable films may be formed with the use of a filler, such as described above. Filled films may be made breathable by stretching, which causes the polymer to break away from the filler and create microporous passageways. Techniques for forming microporous films are described, for example, in U.S. Pat. No. 7,153,569 to Kaufman, et al., as well as U.S. Application Publication Nos. 2005/0208294 to Kaufman, et al. and 2006/0149199 to Topolkaraev, et al., all of which are incorporated herein in their entirety by reference thereto for all purposes. When employed to initiate the formation of micropores, the total filler content in the film may range from about 15 wt. % to about 75 wt. %, in some embodiments, from about 20 wt. % to about 70 wt. %, and in some embodiments, from about 25 wt. % to about 65 wt. %. Likewise, the thermoplastic composition described above may constitute from about 25 wt. % to about 85 wt. %, in some embodiments, from about 30 wt. % to about 80 wt. %, and in some embodiments, from about 35 wt. % to about 75 wt. % of the film.

In embodiments in which it is desired to impart breathability, the film may exhibit a water vapor transmission rate (WVTR) of about 800 grams/m$^2$-24 hours or more, in some embodiments about 1,000 grams/m$^2$-24 hours or more, in some embodiments about 1,200 grams/m$^2$-24 hours or more, and in some embodiments, from about 1,500 to about 10,000 grams/m$^2$-24 hours. The film may also be liquid impermeable so that it limits the amount of liquid water that passes therethrough upon the application of pressure. More particularly, the film may resists a hydrostatic pressure ("hydrohead") of about 50 millibar or more, in some embodiments about 70 millibar or more, in some embodiments about 80 millibar or more, and in some embodiments, about 100 millibar or more without allowing liquid water to pass.

The elastic film of the present invention may be used in a wide variety of applications. For example, as indicated above, the film may be used in an absorbent article. An "absorbent article" generally refers to any article capable of absorbing water or other fluids. Examples of some absorbent articles include, but are not limited to, personal care absorbent articles, such as diapers, training pants, absorbent underpants, incontinence articles, feminine hygiene products (e.g., sanitary napkins, pantiliners, etc.), swim wear, baby wipes, and so forth; medical absorbent articles, such as garments, fenestration materials, underpads, bedpads, bandages, absorbent drapes, and medical wipes; food service wipers; clothing articles; and so forth. Several examples of such absorbent articles are described in U.S. Pat. No. 5,649,916 to DiPalma, et al.; U.S. Pat. No. 6,110,158 to Kielpikowski; U.S. Pat. No. 6,663,611 to Blaney, et al., which are incorporated herein in their entirety by reference thereto for all purposes. Still other suitable articles are described in U.S. Patent Application Publication No. 2004/0060112 A1 to Fell et al., as well as U.S. Pat. No. 4,886,512 to Damico et al.; U.S. Pat. No. 5,558,659 to Sherrod et al.; U.S. Pat. No. 6,888,044 to Fell at al.; and U.S. Pat. No. 6,511,465 to Freiburger et al., all of which are incorporated herein in their entirety by reference thereto for all purposes. Materials and processes suitable for forming such absorbent articles are well known to those skilled in the art.

Materials and processes suitable for forming such absorbent articles are well known to those skilled in the art. Typically, absorbent articles include a substantially liquid-impermeable layer (e.g., outer cover), a liquid-permeable layer (e.g., bodyside liner, surge layer, etc.), and an absorbent core. In one particular embodiment, the composite of the present invention may be used in providing elastic waist, leg cuff/gasketing, stretchable ear, side panel or stretchable outer cover applications.

Figure 2:
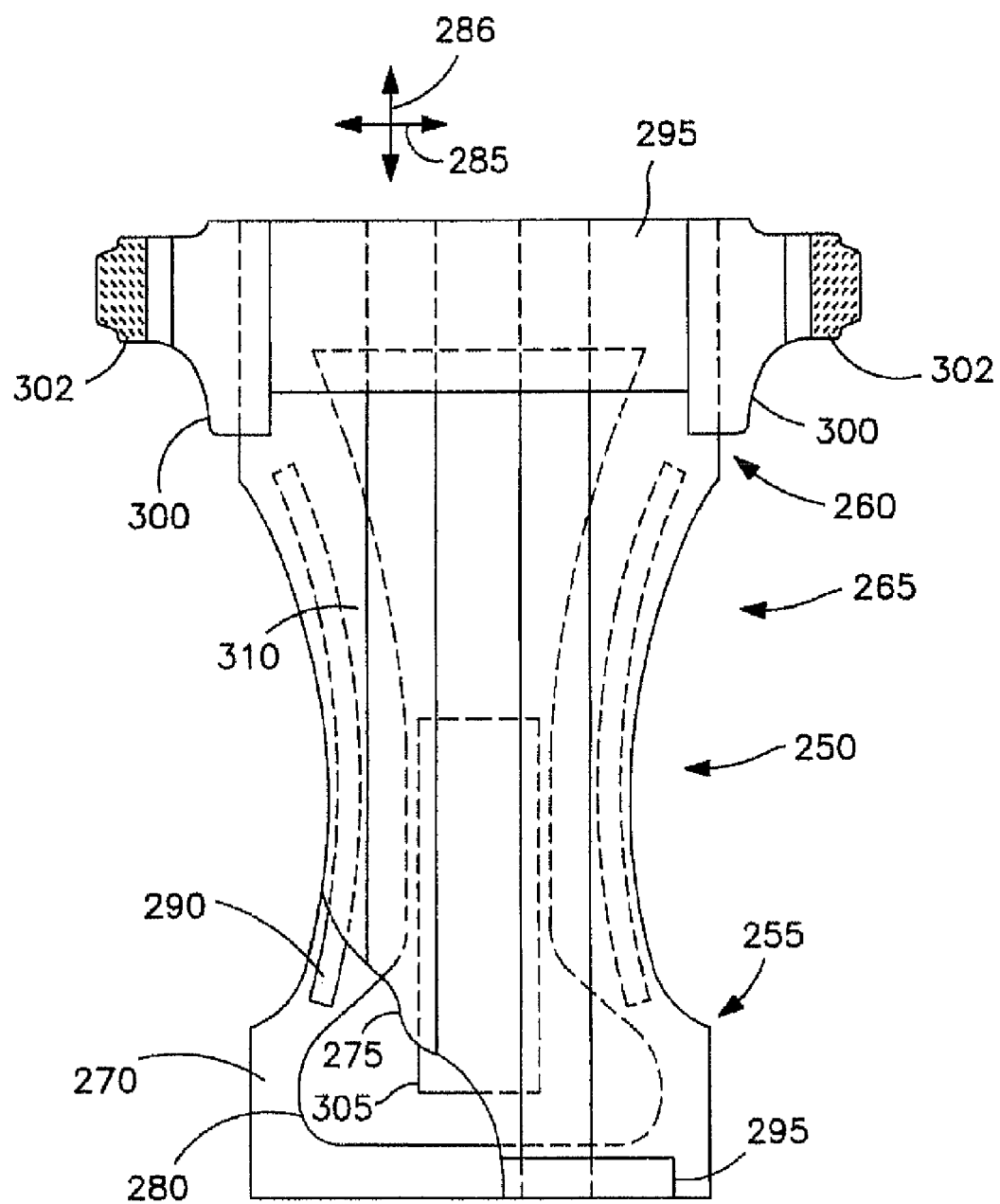
FIG. 2 is a perspective view of an absorbent article that may be formed according to one embodiment of the present invention.

Various embodiments of an absorbent article that may be formed according to the present invention will now be described in more detail. Referring to FIG. 2, for example, one embodiment of a disposable diaper 250 is shown that generally defines a front waist section 255, a rear waist section 260, and an intermediate section 265 that interconnects the front and rear waist sections. The front and rear waist sections 255 and 260 include the general portions of the diaper which are constructed to extend substantially over the wearer's front and rear abdominal regions, respectively, during use. The intermediate section 265 of the diaper includes the general portion of the diaper that is constructed to extend through the wearer's crotch region between the legs. Thus, the intermediate section 265 is an area where repeated liquid surges typically occur in the diaper.

The diaper 250 includes, without limitation, an outer cover, or backsheet 270, a liquid permeable bodyside liner, or topsheet, 275 positioned in facing relation with the backsheet 270, and an absorbent core body, or liquid retention structure, 280, such as an absorbent pad, which is located between the backsheet 270 and the topsheet 275. The backsheet 270 defines a length, or longitudinal direction 286, and a width, or lateral direction 285 which, in the illustrated embodiment, coincide with the length and width of the diaper 250. The liquid retention structure 280 generally has a length and width that are less than the length and width of the backsheet 270, respectively. Thus, marginal portions of the diaper 250, such as marginal sections of the backsheet 270 may extend past the terminal edges of the liquid retention structure 280. In the illustrated embodiments, for example, the backsheet 270 extends outwardly beyond the terminal marginal edges of the liquid retention structure 280 to form side margins and end margins of the diaper 250. The topsheet 275 is generally coextensive with the backsheet 270 but may optionally cover an area that is larger or smaller than the area of the backsheet 270, as desired.

To provide improved fit and to help reduce leakage of body exudates from the diaper 250, the diaper side margins and end margins may be elasticized with suitable elastic members, as further explained below. For example, as representatively illustrated in FIG. 2, the diaper 250 may include leg elastics 290 constructed to operably tension the side margins of the diaper 250 to provide elasticized leg bands which can closely fit around the legs of the wearer to reduce leakage and provide improved comfort and appearance. Waist elastics 295 are employed to elasticize the end margins of the diaper 250 to provide elasticized waistbands. The waist elastics 295 are configured to provide a resilient, comfortably close fit around the waist of the wearer. The elastic film of the present invention may be suitable for use as the leg elastics 290 and waist elastics 295.

As is known, fastening means, such as hook and loop fasteners, may be employed to secure the diaper 250 on a wearer. Alternatively, other fastening means, such as buttons, pins, snaps, adhesive tape fasteners, cohesives, fabric-and-loop fasteners, or the like, may be employed. In the illustrated embodiment, the diaper 250 includes a pair of side panels 300 (or ears) to which the fasteners 302, indicated as the hook portion of a hook and loop fastener, are attached. Generally, the side panels 300 are attached to the side edges of the diaper in one of the waist sections 255, 260 and extend laterally outward therefrom. The side panels 300 may be elasticized or otherwise rendered elastomeric by use of a latently elastic materials of the present invention. Examples of absorbent articles that include elasticized side panels and selectively configured fastener tabs are described in PCT Patent Application WO 95/16425 to Roessler; U.S. Pat. No. 5,399,219 to Roessler et al.; U.S. Pat. No. 5,540,796 to Fries; and U.S. Pat. No. 5,595,618 to Fries, each of which is incorporated herein in its entirety by reference thereto for all purposes.

The diaper 250 may also include a surge management layer 305, located between the topsheet 275 and the liquid retention structure 280, to rapidly accept fluid exudates and distribute the fluid exudates to the liquid retention structure 280 within the diaper 250. The diaper 250 may further include a ventilation layer (not illustrated), also called a spacer, or spacer layer, located between the liquid retention structure 280 and the backsheet 270 to insulate the backsheet 270 from the liquid retention structure 280 to reduce the dampness of the garment at the exterior surface of a breathable outer cover, or backsheet, 270. Examples of suitable surge management layers 305 are described in U.S. Pat. No. 5,486,166 to Bishop and U.S. Pat. No. 5,490,846 to Ellis.

As representatively illustrated in FIG. 2, the disposable diaper 250 may also include a pair of containment flaps 310 which are configured to provide a barrier to the lateral flow of body exudates. The containment flaps 310 may be located along the laterally opposed side edges of the diaper adjacent the side edges of the liquid retention structure 280. Each containment flap 310 typically defines an unattached edge that is configured to maintain an upright, perpendicular configuration in at least the intermediate section 265 of the diaper 250 to form a seal against the wearer's body. The containment flaps 310 may extend longitudinally along the entire length of the Liquid retention structure 280 or may only extend partially along the length of the liquid retention structure. When the containment flaps 310 are shorter in length than the liquid retention structure 280, the containment flaps 310 can be selectively positioned anywhere along the side edges of the diaper 250 in the intermediate section 265. Such containment flaps 310 are generally well known to those skilled in the art. For example, suitable constructions and arrangements for containment flaps 310 are described in U.S. Pat. No. 4,704,116 to Enloe.

The diaper 250 may be of various suitable shapes. For example, the diaper may have an overall rectangular shape, T-shape or an approximately hour-glass shape. In the shown embodiment, the diaper 250 has a generally I-shape. Other suitable components which may be incorporated on absorbent articles of the present invention may include waist flaps and the like which are generally known to those skilled in the art. Examples of diaper configurations suitable for use in connection with the elastic film of the present invention that may include other components suitable for use on diapers are described in U.S. Pat. No. 4,798,603 to Meyer et al.; U.S. Pat. No. 5,176,668 to Bernardin; U.S. Pat. No. 5,176,672 to Bruemmer et al.; U.S. Pat. No. 5,192,606 to Proxmire et al.; and U.S. Pat. No. 5,509,915 to Hanson et al., which are incorporated herein in their entirety by reference thereto for all purposes.

The various regions and/or components of the diaper 250 may be assembled together using any known attachment mechanism, such as adhesive, ultrasonic, thermal bonds, etc. Suitable adhesives may include, for instance, hot melt adhesives, pressure-sensitive adhesives, and so forth. When utilized, the adhesive may be applied as a uniform layer, a patterned layer, a sprayed pattern, or of any separate lines, swirls or dots. In the illustrated embodiment, for example, the topsheet 275 and backsheet 270 may be assembled to each other and to the liquid retention structure 280 with lines of adhesive, such as a hot melt, pressure-sensitive adhesive. Similarly, other diaper components, such as the elastic members 290 and 295, fastening members 302, and surge layer 305 may be assembled into the article by employing the above-identified attachment mechanisms.

Although various configurations of a diaper have been described above, it should be understood that other diaper and absorbent article configurations are also included within the scope of the present invention. In addition, the present invention is by no means limited to diapers. In fact, several examples of absorbent articles are described in U.S. Pat. No. 5,649,916 to DiPalma, et al.; U.S. Pat. No. 6,110,158 to Kielpikowski; U.S. Pat. No. 6,663,611 to Blaney, et al., which are incorporated herein in their entirety by reference thereto for all purposes. Further, other examples of personal care products that may incorporate such materials are training pants (such as in side panel materials) and feminine care products. By way of illustration only, training pants suitable for use with the present invention and various materials and methods for constructing the training pants are disclosed in U.S. Pat. No. 6,761,711 to Fletcher et al,; U.S. Pat. No. 4,940,464 to Van Gompel et al.; U.S. Pat. No. 5,766,389 to Brandon et al.; and U.S. Pat. No. 6,645,190 to Olson et al., which are incorporated herein in their entirety by reference thereto for all purposes.

The present invention may be better understood with reference to the following examples.

Test Methods

Tensile Properties:

The strip tensile strength values were determined in substantial accordance with ASTM Standard D-5034. A constant-rate-of-extension type of tensile tester was employed. The tensile testing system was a Sintech 1/D tensile tester, which is available from MTS Systems Corp. The tensile tester was equipped with TESTWORKS 4.08B software from MTS Systems Corp. to support the testing. An appropriate load cell was selected so that the tested value fell within the range of 10-90% of the full scale load. The film samples were initially cut into dog-bone shapes with a center width of 3.0 mm before testing. The samples were held between grips having a front and back face measuring 25.4 millimeters×76 millimeters. The grip faces were rubberized, and the longer dimension of the grip was perpendicular to the direction of pull, The grip pressure was pneumatically maintained at a pressure of 40 pounds per square inch. The tensile test was run using a gauge length of 18.0 millimeters and a break sensitivity of 40%. Five samples were tested by applying the test load along the machine-direction and five samples were tested by applying the test load along the cross direction. During the test, samples were stretched at a crosshead speed of abut 127 millimeters per minute until breakage occurred. The modulus, peak stress, elongation (Le., % strain at peak load), and elongation were measured.

Cycle Testing

The materials were tested using a cyclical testing procedure to determine percent set. In particular, 1-cycle testing was utilized to 100% defined elongation. The testing was done on a Sintech Corp. constant rate of extension tester 1/D equipped with TESTWORKS 4.08B software from MTS Corporation to support the testing. The test was conducted under ambient conditions. For this test, the sample size was 1 inches (2.54 centimeters) in the cross-machine direction by 3 inches (7.6 centimeter) in the machine direction. Before testing, the net gauge film length was 51 millimeters. The grip size was 3 inches (7.6 centimeters) in width and the grip separation was 4 inches. The samples were loaded such that the machine direction of the sample was in the vertical direction. A preload of approximately 20 to 30 grams was set. The test pulled the sample to 100% elongation at a speed of 20 inches (50.8 centimeters) per minute, held the sample in an elongated state for 30 seconds, and then returned the sample to zero elongation at a speed of 20 inches (50.8 centimeters) per minute. Thereafter, the film length was immediately measured and again measured in 10, 20, and 30 minutes. The percent that did not recover ("percent set") was determined by subtracting the length of the film 30 minutes after cycle testing from the original length of the film, and then dividing this number by the original length of the film.

Materials Employed

Native corn starch was obtained from Cargill.
Glycerol was obtained from Cognis Corp.
ECOFLEX® F BX 7011 was obtained from BASF Corp.
EXCEL P-40S is a nonionic surfactant obtained from Kao Corp.
VISTAMAXX™ 1120 and 6102 are metallocene-catalyzed, ethylene/propylene copolymers obtained from Exxonmobil Corp.
ESTANE™ 58245 is an aromatic, polyether-based thermoplastic polyurethane, produced by Noveon and later by Lubrizol Advanced Materials. In the Examples below, the letter "N" represents the resin purchased from Noveon and the letter "L" represents the resin purchased from Lubrizol. The polyurethane has a $T_g$ of −37° C. and a $T_m$ of 135-139° C.
DESMOPAN™ DP 9370 is an aromatic polyether-based thermoplastic polyurethane obtained from Bayer MaterialScience. It has a $T_g$ of −70° C. and a $T_m$ of 188-199° C.

EXAMPLE 1

A starch-based blend was formed from 73.5 wt. % native corn starch, 1.5 wt. % Excel P-40S, and 25 wt. % glycerin. These components were fed into a co-rotating twin screw extruder (ZSK-30, Werner and Pfleiderer Corporation, Ramsey, N.J.). The extruder diameter was 30 mm and the length of the screws was up to 1328 mm. The extruder has 14 barrels, numbered consecutively 1 to 14 from the feed hopper to the die. The temperature profile of the seven (7) heating zones of the extruder was 70° C., 85° C., 140° C., 145° C., 150° C., 150° C., and 145° C., respectively. The screw speed was set at 160 rpm to achieve a torque of between 31-36% and a $P_{melt}$ of 460~480 psi.

EXAMPLE 2

A starch-based blend was formed from 33.1 wt. % native corn starch, 0.7 wt. % Excel P-40S, 11.2 wt. % glycerin, and 55 wt. % ECOFLEX® F BX 7011. These components were fed into a co-rotating twin screw extruder (ZSK-30, Werner and Pfleiderer Corporation, Ramsey, N.J.). The extruder diameter was 30 mm and the length of the screws was up to 1328 mm. The extruder has 14 barrels, numbered consecutively 1 to 14 from the feed hopper to the die. The temperature profile of the seven (7) heating zones of the extruder was 70° C., 85° C., 140° C., 145° C., 150° C., 150° C., and 156° C., respectively. The screw speed was set at 160 rpm to achieve a torque of between 32-38% and a $P_{melt}$ of 220~230 psi.

EXAMPLES 3-19

The thermoplastic blend of Example 2 was then dry blended with various elastomers (VISTAMAXX™ 1120, VISTAMAXX™ 6102, DESMOPAN™ DP9730A, and ESTANE™ 58245) at various concentrations. Films were cast by adding the mixture to a gravimetric feeder (K-Tron America, Pitman, N.J., Model KCM-2) that fed the blends into a Prism USALAB 16 Twin Screw Extruder (Thermo Electron Corp., Stone, England). The extruder speed was set at 150 rpm. A vent was also provided at zone 9 to release steam generated due to the presence of the moisture in the plasticizer and inherent moisture in the starch. For Examples 3-18, the temperature profile for zones 1 to 10 was 120° C., 130° C., 150° C., 170° C., 180° C. 180° C., 180° C., 175° C., 175° C., and 170° C., respectively. For Example 19, the temperature profile for zones 1 to 10 was 120° C., 130° C., 150° C., 170° C., 175° C., 175° C., 175° C., 175° C., 170° C., and 160° C., respectively. The film compositions are set forth below in Table 1:

TABLE 1

| | Film Composition | | | | |
|---|---|---|---|---|---|
| Example | VISTAMAXX ™ 1120 (wt. %) | VISTAMAXX ™ 6102 (wt. %) | DESMOPAN ™ DP9730A (wt. %) | ESTANE ™ 58245 (wt. %) | Starch Blend of Example 2 (wt. %) |
| 3 | 90 | 0 | 0 | 0 | 10 |
| 4 | 60 | 0 | 0 | 0 | 40 |
| 5 | 30 | 0 | 0 | 0 | 70 |
| 6 | 0 | 70 | 0 | 0 | 30 |
| 7 | 0 | 30 | 0 | 0 | 70 |
| 8 | 0 | 0 | 70 | 0 | 30 |
| 9 | 0 | 0 | 30 | 0 | 70 |
| 10 | 0 | 0 | 0 | 90 | 10 |
| 11 | 0 | 0 | 0 | 80 | 20 |
| 12 | 0 | 0 | 0 | 70 | 30 |
| 13 | 0 | 0 | 0 | 60 | 40 |
| 14 | 0 | 0 | 0 | 50 | 50 |
| 15 | 0 | 0 | 0 | 40 | 40 |
| 16 | 0 | 0 | 0 | 30 | 30 |
| 17 | 0 | 0 | 0 | 20 | 20 |
| 18 | 0 | 0 | 0 | 10 | 10 |
| 19 | 0 | 0 | 0 | 0 | 100 |

Once formed, the tensile properties of the film samples were tested in the manner described above. The results are set forth below in Table 2.

TABLE 2

Mechanical Properties of the Film Samples

| | | | Film Mechanical Properties | | | | | | |
|---|---|---|---|---|---|---|---|---|---|
| | | | Film Thickness | | Modulus (MPa) | | Peak Stress (MPa) | | Elongation (%) | |
| Sample No. | Sample Description | Composition | MD (mil) | CD (mil) | MD | CD | MD | CD | MD | CD |
| Example 3 | VM 1120/Example 2 | 90/10 | 1.9 | 1.7 | 7.6 | 8.5 | 22.8 | 17.2 | 741.5 | 939.6 |
| Example 4 | VM 1120/Example 2 | 60/40 | 2.5 | 2.0 | 11.3 | 10.1 | 20.7 | 10.9 | 813.0 | 859.1 |
| Example 5 | VM 1120/Example 2 | 30/70 | 2.5 | 1.8 | 15.3 | 10.9 | 21.8 | 11.4 | 837.0 | 753.7 |
| Example 6 | VM 6120/Example 2 | 70/30 | 2.5 | 2.4 | 8.6 | 5.7 | 14.6 | 15.2 | 637.5 | 1000.6 |
| Example 7 | VM 6120/Example 2 | 30/70 | 2.5 | 2.2 | 18.5 | 17.4 | 22.9 | 13.7 | 808.3 | 819.3 |
| Example 8 | DP9730A/Example 2 | 70/30 | 2.4 | 2.2 | 12.7 | 8.3 | 45.7 | 30.0 | 750.3 | 774.8 |
| Example 9 | DP9730A/Example 2 | 30/70 | 1.9 | 1.7 | 26.1 | 24.2 | 36.4 | 26.8 | 778.3 | 839.5 |
| Example 10 | Estane/Example 2 | 90/10 | 2.6 | 1.9 | 16.1 | 9.6 | 26.8 | 22.2 | 579.6 | 600.1 |
| Example 11 | Estane/Example 2 | 80/20 | 2.0 | 2.0 | 7.8 | 9.7 | 32.3 | 22.7 | 661.2 | 754.1 |
| Example 12 | Estane/Example 2 | 70/30 | 1.9 | 1.9 | 11.5 | 11.5 | 21.9 | 21.9 | 740.5 | 740.5 |
| Example 13 | Estane/Example 2 | 60/40 | 2.1 | 2.1 | 13.8 | 9.4 | 31.0 | 21.6 | 687.4 | 746.5 |
| Example 14 | Estane/Example 2 | 50/50 | 2.2 | 2.0 | 22.1 | 17.3 | 30.2 | 24.3 | 693.2 | 839.9 |
| Example 15 | Estane/Example 2 | 40/60 | 2.0 | 1.9 | 22.7 | 20.1 | 27.2 | 19.9 | 657.5 | 755.5 |
| Example 16 | Estane/Example 2 | 30/70 | 1.6 | 1.6 | 22.7 | 18.4 | 24.8 | 16.8 | 596.4 | 702.2 |
| Example 17 | Estane/Example 2 | 20/80 | 2.1 | 1.9 | 19.4 | 19.1 | 24.9 | 15.3 | 679.7 | 667.4 |
| Example 18 | Estane/Example 2 | 10/90 | 1.9 | 1.8 | 24.5 | 23.8 | 20.7 | 14.1 | 592.1 | 626.6 |
| Example 19 | Estane/Example 2 | 0/100 | 1.6 | 1.4 | 21.7 | 21.4 | 20.1 | 13.2 | 631.6 | 597.6 |

As indicated, the film samples of Examples 3-19 had excellent elongation properties.

Furthermore, to assess film elasticity, the film samples were also subjected to cycle testing as described above. The results are set forth below in Table 3.

TABLE 3

Film Mechanical Stretch and Recovery

| Sample No. | Sample Description | Orientation | Original | After Test (mm) | After 10 min (mm) | After 20 min (mm) | After 30 min (mm) | % Not Recovered |
|---|---|---|---|---|---|---|---|---|
| Example 3 | VM 1120/Example 2 (90/10) | MD | 51.0 | 51.7 | 50.7 | 50.3 | 50.0 | −2.0 |
| | | CD | 51.0 | 51.3 | 50.0 | 50.0 | 50.0 | −2.0 |
| Example 4 | VM 1120/Example 2 (60/40) | MD | 51.0 | 58.3 | 56.3 | 56.3 | 56.3 | 10.4 |
| | | CD | 51.0 | 57.7 | 55.7 | 55.3 | 55.3 | 8.4 |
| Example 5 | VM 1120/Example 2 (30/70) | MD | 51.0 | 66.3 | 63.3 | 63.3 | 63.0 | 23.5 |
| | | CD | 51.0 | 70.6 | 66.0 | 66.3 | 66.3 | 30.0 |
| Example 6 | VM 6120/Example 2 (70/30) | MD | 51.0 | 54.3 | 53.0 | 52.3 | 52.3 | 2.5 |
| | | CD | 51.0 | 52.3 | 51.0 | 51.0 | 51.0 | 0.0 |
| Example 7 | VM 6120/Example 2 (30/70) | MD | 51.0 | 68.0 | 65.0 | 64.7 | 64.7 | 26.9 |
| | | CD | 51.0 | 69.3 | 66.7 | 66.0 | 66.0 | 29.4 |
| Example 8 | DP9730A/Example 2 (70/30) | MD | 51.0 | 52.3 | 51.0 | 51.0 | 51.0 | 0.0 |
| | | CD | 51.0 | 51.0 | 50.0 | 50.0 | 50.0 | −2.0 |
| Example 9 | DP9730A/Example 2 (30/70) | MD | 51.0 | 65.3 | 62.3 | 62.3 | 62.3 | 22.2 |
| | | CD | 51.0 | 66.3 | 63.7 | 63.0 | 62.7 | 22.9 |
| Example 10 | Estane/Example 2 (90/10) | MD | 51.0 | 52.0 | 50.7 | 50.7 | 50.7 | −0.7 |
| | | CD | 51.0 | 52.0 | 51.0 | 51.0 | 51.0 | 0.0 |
| Example 11 | Estane/Example 2 (80/20) | MD | 51.0 | 53.0 | 51.7 | 51.0 | 51.0 | 0.0 |
| | | CD | 51.0 | 52.0 | 51.0 | 51.3 | 51.0 | 0.0 |
| Example 12 | Estane/Example 2 (70/30) | MD | 51.0 | 53.7 | 52.0 | 52.0 | 52.0 | 2.0 |
| | | CD | 51.0 | 54.3 | 52.3 | 52.0 | 52.0 | 2.0 |
| Example 13 | Estane/Example 2 (60/40) | MD | 51.0 | 57.0 | 55.0 | 55.0 | 55.0 | 7.8 |
| | | CD | 51.0 | 57.0 | 55.3 | 54.7 | 54.3 | 6.5 |
| Example 14 | Estane/Example 2 (50/50) | MD | 51.0 | 60.3 | 57.7 | 57.0 | 56.7 | 11.1 |
| | | CD | 51.0 | 66.3 | 62.7 | 61.3 | 61.3 | 20.3 |
| Example 15 | Estane/Example 2 (40/60) | MD | 51.0 | 64.7 | 61.7 | 61.3 | 61.0 | 19.6 |
| | | CD | 51.0 | 68.0 | 63.7 | 64.0 | 63.7 | 24.8 |
| Example 16 | Estane/Example 2 (30/70) | MD | 51.0 | 65.0 | 62.3 | 62.0 | 62.0 | 21.6 |
| | | CD | 51.0 | 68.7 | 65.3 | 65.3 | 65.3 | 28.1 |
| Example 17 | Estane/Example 2 (20/80) | MD | 51.0 | 68.3 | 66.7 | 66.3 | 66.3 | 30.1 |
| | | CD | 51.0 | 70.3 | 67.7 | 68.0 | 67.7 | 32.7 |
| Example 18 | Estane/Example 2 (10/90) | MD | 51.0 | 72.0 | 69.3 | 68.3 | 68.3 | 34.0 |
| | | CD | 51.0 | 70.3 | 67.0 | 67.0 | 66.7 | 30.7 |

TABLE 3-continued

Film Mechanical Stretch and Recovery

| Sample No. | Sample Description | Orientation | Original | After Test (mm) | After 10 min (mm) | After 20 min (mm) | After 30 min (mm) | % Not Recovered |
|---|---|---|---|---|---|---|---|---|
| Example 19 | Example 2 | MD | 51.0 | 73.7 | 71.3 | 71.3 | 70.7 | 38.6 |
| | | CD | 51.0 | 80.3 | 76.7 | 76.0 | 76.0 | 49.0 |

As indicated, the permanent set was very low. For instance, Example 4 exhibited a permanent set of 8% and 10% in the machine direction and cross-machine direction, respectively, even though it possessed 40 wt. % of a non-elastomeric component.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. An elastic film comprising a thermoplastic composition, wherein the thermoplastic composition comprises at least one starch polymer constituting from about 1 wt. % to about 30 wt. % of the polymer content of the film, at least one elastomeric polymer constituting from about 30 wt. % to about 95 wt. % of the polymer content of the film, wherein the elastomeric polymer includes a metallocene-catalyzed ethylene/α-olefin copolymer, a metallocene-catalyzed propylene/α-olefin copolymer, or a combination thereof having a density of from about 0.85 g/cm$^3$ to about 0.89 g/cm$^3$, a thermoplastic polyurethane synthesized from a polyol and an organic diisocyanate and having a melting point of from about 75° C. to about 250° C., or a combination thereof; and at least one plasticizer constituting from about 0.1 wt. % to about 30 wt. % of the film, wherein the weight ratio of elastomeric polymers to starch polymers in the film is from about 1 to about 10, the elastic film exhibiting an elongation in the machine direction and cross-machine direction of about 250% or more.

2. The elastic film of claim 1, wherein the starch polymer is a native starch.

3. The elastic film of claim 2, wherein the native starch has an amylose content of from about 10% to about 40% by weight.

4. The elastic film of claim 2, wherein the native starch has a number average molecular weight ranging from about 50,000 to about 1,000,000 grams per mole.

5. The elastic film of claim 1, wherein the polyol includes a polyether polyol and the organic diisocyanate includes an aromatic diisocyanate.

6. The elastic film of claim 1, wherein the plasticizer includes a polyhydric alcohol.

7. The elastic film of claim 6, wherein the polyhydric alcohol includes a polyol.

8. The elastic film of claim 1, wherein starch polymers constitute from about 5 wt % to about 20 wt. % of the polymer content of the film, elastomeric polymers constitute from about 50 wt. % to about 80 wt. % of the polymer content of the film, and wherein the weight ratio of elastomeric polymers to starch polymers in the film is from about 3 to about 6.

9. The elastic film of claim 1, wherein plasticizers constitute from about 1 wt. % to about 10 wt. % of the film.

10. The elastic film of claim 1, wherein the film further comprises a synthetic biodegradable polyester.

11. The elastic film of claim 10, wherein the synthetic biodegradable polyester includes a polycaprolactone, polyesteramide, modified polyethylene terephthalate, polylactic acid or a copolymer or terpolymer thereof, polyglycolic acid, polyalkylene carbonate, polyhydroxyalkanoate, poly-3-hydroxybutyrate, poly-3-hydroxyvalerate, poly-3-hydroxybutyrate-co-4-hydroxybutyrate, poly-3-hydroxybutyrate-co-3-hydroxyvalerate copolymer, poly-3-hydroxybutyrate-co-3-hydroxyhexanoate, poly-3-hydroxybutyrate-co-3-hydroxyoctanoate, poly-3-hydroxybutyrate-co-3-hydroxydecanoate, poly-3-hydroxybutyrate-co-3-hydroxyoctadecanoate, succinate-based aliphatic polymer, aromatic polyester, modified aromatic polyester, aliphatic-aromatic copolyester, or a combination thereof.

12. The elastic film of claim 10, wherein synthetic biodegradable polyesters constitute from about 5% to about 60% of the elastic film.

13. The elastic film of claim 1, wherein the film is liquid impermeable.

14. The elastic film of claim 1, wherein the elastic film exhibits an elongation in the machine direction and cross-machine direction of from about 500% to about 2500%.

15. The elastic film of claim 1, wherein the elastic film exhibits a Young's modulus of elasticity in the machine direction and cross-machine direction of from about 1 to about 100 Megapascals.

16. The elastic film of claim 1, wherein the elastic film exhibits an ultimate tensile strength in the machine direction and cross-machine direction of from about 1 to about 100 Megapascals.

17. The elastic film of claim 1, wherein the elastic film exhibits permanent set from about 1% to about 30%.

18. The elastic film of claim 1, wherein the elastic film exhibits a percent set in the machine direction of from −2.0 to 26.9.

19. An absorbent article comprising an elastic film, wherein the elastic film comprises at least one starch polymer constituting from about 1 wt. % to about 30 wt. % of the polymer content of the film; at least one elastomeric polymer constituting from about 30 wt. % to about 95 wt. % of the polymer content of the film, wherein the elastomeric polymer includes a metallocene-catalyzed ethylene/α-olefin copolymer, a metallocene-catalyzed propylene/α-olefin copolymer, or a combination thereof having a density of from about 0.85 g/cm$^3$ to about 0.89 g/cm$^3$, a thermoplastic polyurethane synthesized from a polyol and an organic diisocyanate and having a melting point of from about 75° C. to about 250° C., or a combination thereof; and at least one plasticizer constituting from about 0.1 wt. % to about 30 wt. % of the film; wherein the weight ratio of elastomeric polymers to starch polymers in the film is from about 1 to about 10, the elastic film exhibiting an elongation in the machine direction and cross-machine direction of about 250% or more.

20. The absorbent article of claim 19, wherein the absorbent article contains a body portion that includes a liquid permeable topsheet, a generally liquid impermeable backsheet, and an absorbent core positioned between the backsheet and the topsheet.

21. The absorbent article of claim 20, wherein the backsheet includes the elastic film.

22. The absorbent article of claim 20, further comprising one or more elastic members that include the elastic film.

23. The absorbent article of claim 22, wherein the elastic members are leg elastics, waist elastics, or a combination thereof.

24. The absorbent article of claim 19, wherein the elastic film exhibits a percent set in the machine direction of from −2.0 to 26.9.

25. A method for forming an elastic film, the method comprising melt blending a composition comprising at least one starch polymer constituting from about 1 wt. % to about 30 wt. % of the polymer content of the film, at least one elastomeric polymer constituting from about 30 wt. % to about 95 wt. % of the polymer content of the film, wherein the elastomeric polymer includes a metallocene-catalyzed ethylene/α-olefin copolymer, a metallocene-catalyzed propylene/α-olefin copolymer, or a combination thereof having a density of from about a $0.85 g/cm^3$ to about $0.89 g/cm^3$, a thermoplastic polyurethane synthesized from a polyol and an organic diisocyanate and having a melting point of from about 75° C. to about 250° C. or a combination thereof; and at least one plasticizer constituting from about 0.1 wt. % to about 30 wt. % of the film, wherein the weight ratio of elastomeric polymers to starch polymers in the film is from about 1 to about 10, the elastic film exhibiting an elongation in the machine direction and cross-machine direction of about 250% or more, the method further comprising extruding the composition onto a surface to form a film.

26. The method of claim 25, wherein melt blending occurs at a temperature of from about 80° C. to about 300° C.

27. The method of claim 25, further comprising stretching the film in the machine direction, the cross-machine direction, or both.

\* \* \* \* \*

UNITED STATES PATENT AND TRADEMARK OFFICE
CERTIFICATE OF CORRECTION

Page 1 of 1

PATENT NO. : 8,889,945 B2
APPLICATION NO. : 12/962749
DATED : November 18, 2014
INVENTOR(S) : James H. Wang and Bo Shi It is certified that error appears in the above-identified patent and that said Letters Patent is hereby corrected as shown below:

In the Claims

Claim 25 (column 26, line 3)

"...from about a 0.85 g/cm3 to about 0.89 g/cm3, a thermoplastic,..." should read --from about 0.85 g/cm3 to about 0.89 g/cm3, a thermoplastic--

Signed and Sealed this
Fourteenth Day of July, 2015

Michelle K. Lee
*Director of the United States Patent and Trademark Office*